(12) United States Patent
Zamora et al.

(10) Patent No.: US 6,596,699 B2
(45) Date of Patent: Jul. 22, 2003

(54) NUCLEIC ACID COATING COMPOSITIONS AND METHODS

(75) Inventors: Paul O. Zamora, Gaithersburg, MD (US); Ray Tsang, Salt Lake City, UT (US); Shigemasa Osaki, Sandy, UT (US)

(73) Assignee: BioSurface Engineering Technologies, Inc., College Park, MD (US)

( * ) Notice: Subject to any disclaimer, the term of this patent is extended or adjusted under 35 U.S.C. 154(b) by 0 days.

(21) Appl. No.: 10/054,091

(22) Filed: Jan. 22, 2002

(65) Prior Publication Data

US 2002/0160098 A1 Oct. 31, 2002

Related U.S. Application Data

(63) Continuation-in-part of application No. 09/629,059, filed on Jul. 31, 2000, now Pat. No. 6,342,591, which is a continuation-in-part of application No. 09/399,119, filed on Sep. 20, 1999, now abandoned, which is a continuation of application No. 09/159,276, filed on Sep. 22, 1998, now Pat. No. 5,955,588.

(51) Int. Cl.[7] ............ A61K 31/70; A61K 31/727; A61M 5/32; B01J 13/00; C08B 37/10
(52) U.S. Cl. .............. 514/44; 514/54; 514/55; 514/56; 514/62; 536/3; 536/21; 536/23.1; 536/112; 536/123.1; 523/112; 604/266; 427/2.1; 427/2.24; 427/2.25; 427/2.3
(58) Field of Search .............. 514/44, 54, 56, 514/55, 62; 536/21, 3, 112, 23.1, 123.1; 523/112; 604/266; 427/2.1, 2.24, 2.25, 2.3

(56) References Cited

U.S. PATENT DOCUMENTS

| | | | |
|---|---|---|---|
| 3,522,346 A | 7/1970 | Chang | 424/35 |
| 3,618,613 A | 11/1971 | Schulte | 128/348 |
| 3,810,781 A | 5/1974 | Eriksson et al. | 117/47 A |
| 4,046,725 A | 9/1977 | Pusineri | 260/9 |
| 4,073,723 A | 2/1978 | Swank et al. | 210/23 R |
| 4,118,485 A | 10/1978 | Eriksson et al. | 424/183 |
| 4,219,520 A | 8/1980 | Kline | 264/129 |
| 4,254,180 A | 3/1981 | Kline | 428/323 |
| 4,265,927 A | 5/1981 | Eriksson et al. | 427/2 |
| 4,378,224 A | 3/1983 | Nimni et al. | 8/94.11 |
| 4,448,691 A | 5/1984 | Davis | 210/656 |
| 4,779,641 A | 10/1988 | Charm et al. | 137/238 |
| 4,833,200 A | 5/1989 | Noishiki et al. | 525/54.2 |
| 4,865,870 A | 9/1989 | Hu et al. | 427/2 |
| 4,871,357 A | 10/1989 | Hsu et al. | 604/266 |
| 4,871,437 A | 10/1989 | Marschman et al. | 204/291 |
| 4,921,483 A | 5/1990 | Wijay et al. | 604/96 |
| 5,019,096 A | 5/1991 | Fox, Jr. et al. | 623/1 |
| 5,047,020 A | 9/1991 | Hsu | 604/266 |
| 5,067,491 A | 11/1991 | Taylor, II et al. | 128/748 |
| 5,069,899 A | 12/1991 | Whitbourne et al. | 424/56 |
| 5,135,516 A | 8/1992 | Sahtjian et al. | 604/265 |
| 5,166,320 A | 11/1992 | Wu et al. | 530/395 |
| 5,308,617 A | 5/1994 | Halluin | 424/94.64 |
| 5,334,379 A | 8/1994 | Pillai et al. | 424/85.2 |
| 5,336,518 A | 8/1994 | Narayanan et al. | 623/1 |
| 5,338,770 A | 8/1994 | Winters et al. | 523/112 |
| 5,383,927 A | 1/1995 | De Goicoechea et al. | 623/1 |
| 5,391,580 A | 2/1995 | Douglas et al. | 521/27 |
| 5,463,010 A | 10/1995 | Hu et al. | 528/25 |
| 5,541,167 A | 7/1996 | Hsu et al. | 514/56 |
| 5,614,503 A | 3/1997 | Chaudhary et al. | 514/44 |
| 5,635,383 A | 6/1997 | Wu et al. | 435/172.3 |
| 5,650,234 A | 7/1997 | Dolence et al. | 428/447 |
| 5,788,959 A | 8/1998 | Singh | 424/85.1 |
| 5,837,533 A | 11/1998 | Boutin | 435/320.1 |
| 5,955,588 A | 9/1999 | Tsang et al. | 536/21 |
| 6,024,918 A | 2/2000 | Hendriks et al. | 422/44 |
| 6,030,954 A | 2/2000 | Wu et al. | 514/44 |
| 6,312,727 B1 | 11/2001 | Schacht et al. | 424/490 |
| 2003/0044514 A1 * | 3/2003 | Richard | 427/2.1 |

FOREIGN PATENT DOCUMENTS

| | | | |
|---|---|---|---|
| GB | 863235 | 3/1961 | |
| JP | 52072782 A * | 6/1977 | C08G/81/00 |
| WO | WO 92/05778 | 4/1992 | |
| WO | WO 98/20027 | 5/1998 | |
| WO | WO 99/55315 | 4/1999 | |
| WO | WO 01/81925 A1 | 1/2001 | |
| WO | WO 01/41674 A1 | 6/2001 | |

OTHER PUBLICATIONS

Published U.S. patent application, publication No. US 2001/0005717 A1; Application No. 09/446,317; Filing Date Jun. 18, 1998; Applicants: Ernst Wagner et al.

Published U.S. patent application, publication No. US 2001/0024829 A1; Application No. 09/753,990; Filing Date Jan. 2, 2001; Applicants: Jon A. Wolff et al.

Shaklee, P.N. et al. *Hydrazinolysis of heparin and other glycosaminoglycans*. Biochem. J. (1984) vol. 217, pp. 187–197.

Nagasawa, K. et al. *[43] De–N–sulfation*. Methods in Carbohydrate Chemistry, vol. VIII (1980) pp. 291–294.

Levy, L. et al. *Chemical and Pharmacological Studies on N–Resulfated Heparin*. Proc. Soc. Expt. Biol and Med. (1962) pp. 901–905.

(List continued on next page.)

*Primary Examiner*—Kathleen K Fonda
(74) *Attorney, Agent, or Firm*—Stephen A. Slusher; Peacock, Myers & Adams, P.C.

(57) ABSTRACT

A nucleic acid coating composition including a polyanion bound, directly or through one or more intermediates, to a medical device surface, with a condensate comprising a polycation and nucleic acid bound to the polyanion, devices incorporating such coating compositions, and methods for making. In one embodiment, a silyl-heparin complex is provided, bound to a medical device surface by hydrophobic interaction with the silyl moiety, with a polycation and nucleic acid condensate bound to the heparin by electrostatic interaction.

33 Claims, 2 Drawing Sheets

OTHER PUBLICATIONS

Polysciences, Inc. Data Sheet #172, Mar. 1991. *TDMA-C–Heparin Coatings for Preparing Antithrombogenic Plastic Surfaces*.

Inoue, Y. et al. *Depolymerization of Heparin with Diazomethane. Structure of N,O–Methylated, Even–Numbered Oligosaccharides Produced by B–Eliminative Cleavage of the 2–Amino–2–Deoxyglycosylic Linkage*. Carbohydrate Research, (1984) vol. 131, pp. 285–300.

Gitel, S.N. et al. *Preparation and Identification of a Population of Antibodies that Recognize Carbodiimide–Modified Heparin*. Blood, (1985) vol. 65, No. 4, pp. 902,911.

Kim, Y.J. et al. *Thermal and Structural Analysis of Heparin–PEO–PDMS–PEO–Heparin Pentablock Copolymers*. Journal of Applied Polymer Science (1994) pp. 1863–1872.

Brown, M.D. et al. *Gene Delivery with Synthetic Carriers—Progress and Problems*. United Kingdom and Ireland Controlled Release Society, Department of Pharmaceutical Sciences, University of Strathclyde, and Department of Medical Oncology, University of Glasgow. Jun. 2001.

Cristiano, R.J. *Targeted Non–Viral Gene Delivery for Cancer Gene Therapy*. Frontiers in Bioscience (Nov. 15, 1998) vol. 3, pp. 1161–1170.

* cited by examiner

NUCLEIC ACID COATING COMPOSITIONS AND METHODS

CROSS-REFERENCE TO RELATED APPLICATIONS

This application is a continuation-in-part application of U.S. patent application Ser. No. 09/629,059, entitled Amphipathic Coating for Modulating Cellular Adhesion Composition and Methods, to Paul O. Zamora, Ray Tsang and Shigemasa Osaki, filed on Jul. 31, 2000, now U.S. Pat. No. 6,342,591; which application is in turn a continuation-in-part application of U.S. patent application Ser. No. 09/399,119, entitled Non-Thrombogenic Coating Compositions and Methods for Using Same, to Ray Tsang and Shigemasa Osaki, filed on Sep. 20, 1999, now abandoned; which application is in turn a continuation patent application of U.S. patent application Ser. No. 09/159,276, filed Sep. 22, 1998, now U.S. Pat. No. 5,955,588, entitled Non-Thrombogenic Coating Compositions and Methods for Using Same, to Ray Tsang and Shigemasa Osaki; and this application is related to PCT/US01/24000, entitled Bioactive Coating Compositions and Methods, to Paul O. Zamora, Shigemasa Osaki and Ray Tsang; and the specification of each of the foregoing is incorporated herein by reference.

BACKGROUND OF THE INVENTION

1. Field of the Invention (Technical Field)

The present invention relates to coatings, methods of making and using coating compositions, and coated contacting surfaces of medical devices, wherein the coating includes a negatively-charged polymeric substrate forming a part of the coating surface, with a condensate complex of nucleic acid and a positively-charged polymer bound thereto by non-covalent means.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

There is a need for localized or regional (loco-regional) delivery of nucleic acids, such as DNA, for use in treatment of a variety of diseases by gene therapy and as a preventative or adjunct to other therapeutic modalities. However, systemic administration of DNA constructs, such as those including adenovirus vectors, frequently results in adverse consequences, and requires a substantially greater amount of gene construct than would be required with effective loco-regional transfection. In addition, for many conditions there is a need for controlled or sustained release of nucleic acids over a period of time, such that the gene construct may be continuously delivered. A number of methods and devices for gene transfection have been developed, but all involve significant limitations. There is thus a need for a biologically compatible method of loco-regional delivery of gene constructs, which may be incorporated and used with traditional implantable medical devices, or may be used with bioresorbable devices.

In the specific field of medical devices, use of medical devices, such as stents, catheters and the like, has been proposed to deliver nucleic acids that encode proteins or peptides directly related to the function of or recognized effects with medical devices. Thus, it has been proposed to utilize a device that delivers nucleic acid that encodes for fibroblast growth factor (FGF), platelet derived growth factor (PDGF), transforming growth factor (TGF), epidermal growth factor (EGF), vascular endothelial growth factor (VEGF), acidic fibroblast growth factor (aFGF), basic fibroblast growth factor (bFGF), fibroblast growth factor-5 (FGF-5) and the like, as disclosed in WO 01/41674, to M. Lahtinen, published Jun. 14, 2001. The WO 01/41674 reference employs a reservoir system for delivering nucleic acids, or alternatively binds nucleic acids, such as plasmids, to a "glue composition" to immobilize the nucleic acids. Also of interest are genes such as nitric oxide synthetase, DNA constructs encoding interleukins, and genes that are introduced for gene-directed pro-drug therapy of cancer such as cytosine deaminase and uracil phosphoribosyltransferase.

It is generally known that nucleic acids, such as DNA, are naturally condensed in the nucleus of cells by histone proteins to form discrete structures termed nucleosomes. Nucleosomes, and the associated DNA, ultimately form chromosomes. There are five major types of histones, termed H1, H2a, H2B, H3, and H4. The histone proteins are rich in basic amino acids that contact negatively charged phosphate groups in DNA. DNA can also be condensed in vitro, through the use of polycations including isolated histones, polyornithine, polylysine, and the like to form a condensate. DNA is a highly negatively charged polymer, due to the repeating phosphate groups along the polymer backbone. With a cationic polymer such as polylysine a condensate is formed, presumptively through an electrostatic interaction between the DNA and polycation. This results in a complex of much smaller size that the original DNA molecule, which complex has exterior and accessible $-NH_2$ charges. Very large genes can be condensed using this method, with genes as large as 45 kilobases employed. The size of a DNA and polycation complex forming a condensate is generally on the order of 50 to 300 nm in diameter, depending in part on the molecular weight of the DNA, size and character of the polycation, polycation molecular weight, salt concentration, temperature and the like. Condensates as small as 12 to 30 nm in diameter have been reported under optimal conditions.

The condensates are generally referred to as polyplexes (DNA/polymer complexes) and are being widely investigated as vehicles for gene therapy. One of the major limitations in polyplex-mediated gene delivery is the low circulation half-life of the polyplexes due to non-specific interactions such as those with extracellular matrices and non-target cell surfaces, clearance by the innate immune system, and aggregation at physiological salt conditions. The result of such non-specific interactions includes deposition in non-target organs such as the lung, as is disclosed in Verbaan F J, Oussoren C, van Dam I M, Takakura Y, Hashida M, Crommelin D J, Hennink W E, Storm G. The fate of poly(2-dimethyl amino ethyl)methacrylate-based polyplexes after intravenous administration. *Int. J. Pharm.* 214:99–101 (2001). Poly(ethylene glycol)-grafted (PEG) cationic polymers have shown promise by increasing the salt and serum stability of the resulting PEGylated polyplexes. However, PEGylation at high densities or PEGylation of low molecular weight cationic polymers usually prevents efficient DNA condensation by interfering with DNA binding.

A number of references disclose use of various systemic gene delivery systems. U.S. Pat. No. 5,166,320, to Wu and Wu, discloses a soluble DNA complex, comprising DNA bound to a polycation, which polycation is in term bound, by means of covalent bonds, to ligand specific for a cell surface receptor. This results in discrete molecular complexes which then bind a cell surface receptor. U.S. Pat. No. 5,614,503, to Chaudhary et al., discloses a nucleic acid transporter comprising a cationic compound having a cationic head group for binding the nucleic acid and a lipid tail for association with a cellular membrane. U.S. Pat. No. 5,837,533, to Boutin, discloses a multifunctional molecular complex including a cationic polyamide component, a fusogenic peptide, and a receptor-specific binding component. U.S. Pat. No. 6,312,727 discloses a synthetic polymer-based carrier vehicle including a cationic polymer forming a condensate with nucleic acid material reacted with a hydrophilic polymer material, resulting in a hydrophilic coating on the condensate. U.S. Patent Application No. 2001/10005717 discloses complexes of nucleic acid and polyethyleneimine, modified with a hydrophilic polymer covalently attached thereto. None of these methods, however, are adaptable to provide coatings for medical devices.

U.S. Pat. No. 5,788,959, to Singh, discloses a drug delivery device which comprises a single-phase matrix of two oppositely charged polymers. However, this device is not a component of a coating, the drugs disclosed therein do not include gene therapy drugs, such as nucleic acids, and no condensate or similar structure is formed.

U.S. Pat. Nos. 5,635,383 and 6,030,954, both to Wu and Wu, discloses a drug delivery formulation that comprises a soluble DNA-carrying complex formed by non-covalently binding a ligand conjugate with DNA. The conjugate, in turn, is formed by bonding receptor-specific ligands such as asialoglycoproteins to polycations such as polylysine through covalent bonds such as disulfide bonds. However, these preparations have not been applied to medical devices, nor were the asialoglyproteins modified to increase adsorption to medical devices.

A simple method of efficiently complexing nucleic acids, such as DNA, RNA and other nucleic acids, including anti-sense compositions and compositions including vectors, to surfaces of medical devices and other implantable devices would have wide applicability.

There remains a need in the art for coating compositions for implantable medical devices that include nucleic acids, and further wherein nucleic acid release can be modulated by the selection of appropriate reactants and components, and which can be applied simply and easily with no specialized equipment or techniques.

A primary object of the present invention is to provide a coating composition for contacting surfaces of implantable medical devices, wherein the composition comprises a heparin and nucleic acid condensate complex.

A further object of the invention is to provide an amphipathic silyl-heparin-nucleic acid condensate coating composition for contacting surfaces of implantable medical devices, which promotes sustained release of nucleic acids.

A further object of the present invention is to provide a cost effective and commercially feasible method for coating polymeric medical devices, including biodegradable medical devices, with a coating comprising nucleic acid condensate molecules.

A further object of the present invention is to provide a cost effective and commercially feasible method for coating polymeric medical devices, including biodegradable medical devices, with a coating comprising a silyl-heparin-nucleic acid condensate molecule composition.

A primary advantage of the present invention is that it provides for coating contacting surfaces of medical devices of complex geometries and surfaces with a durable and low-cost coating including nucleic acids that promotes the desired biological or therapeutic effect, depending on the nucleic acids selected.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (Best Modes For Carrying Out The Invention)

Unless otherwise defined, all technical and scientific terms employed herein have their conventional meaning in the art. As used herein, the following terms have the meanings ascribed to them.

"Alkyl" refers to linear branched or cyclic, saturated or unsaturated $C_{1-18}$ hydrocarbons such as methyl, ethyl, ethenyl, propyl, propenyl, iso-propyl, butyl, iso-butyl, t-butyl, pentyl, cyclopentyl, hexyl, cyclohexyl, octyl, and the like.

"Aryl" refers to unsaturated $C_{6-32}$ hydrocarbon rings that may be substituted from 1–5 times with alkyl, halo, or other aryl groups. Aryl also includes bicyclic aryl groups. Specific examples of aryl groups include but are not limited to phenyl, benzyl, dimethyl phenyl, tolyl, methyl benzyl, dimethyl benzyl, trimethyl phenyl, ethyl phenyl, ethyl benzyl, and the like.

"Heparin" as used herein includes complex carbohydrates or mimetics of complex carbohydrates with properties similar to those of heparin, including heparan sulfate, hyaluronic acid, amino dextran, dextran sulfate, chondroitin sulfate, dermatan sulfate, and the like, including but not limited to a molecules including a mixture of variably sulfated polysaccharide chains composed of repeating units of D-glucosamine and either L-iduronic or D-glucuronic acids, salts of any of the foregoing and derivatives of any of the foregoing.

"Polycation" refers to any polymeric cation that may mediate nucleic acid condensation or compaction. This thus includes linear polycations such as poly-L-lysine, polyornithine, polyarginine and the like. The polymers may be homopolymers, such as polylysine, polyornithine, or polyarginine, or may be heteropolymers, including random polymers formed of lysine, ornithine, arginine and the like. More complex molecules may also be employed as polycations, such as branched or linear polyethylenimine and the like. Any of a variety of naturally occurring nucleic acid binding agents may be employed, such as spermine or spermidine, and are including within the definition of polycation. Protamine can similarly be employed, as can any of a variety of histones. Polyamidoamine dendrimers may similarly be employed, wherein terminal amino groups bind the nucleic acid by electrostatic means, resulting in positively charged condensates. The polycation may be specifically modified to provide optimal characteristics to form the desired condensate. For example, AlkCWK$_{18}$ (a repeating lysine chain of 18 residues followed by a tryptophan and an alkylated cysteine residue) has been reported to form condensates with properties at least equal to polylysine. McKenzie et al., *J. Peptide Res.* 54:311–318 (1999). In general, the polycation is positively charged, and has a net positive charge at about pH 6 to about 8 or has more than about five positively charged residues. The polycation has a higher number of positive charges compared to the number of negative charges. A polycation includes natural nucleic acid-binding proteins and recombinant nucleic acid-binding protein, such as homo- or hetero-polymers of amino acids or synthetic compounds that bind to one or more nucleic acid sequences found within natural or recombinant nucleic acid molecules and results in nucleic acid condensation.

"Polyanion" includes heparin, as defined above, including specifically any polymer that has a negative charge at about pH 6 to about 8 or has more than about five negatively-charged residues. A polyanion has a higher number of negative charges compared to the number of positive charges. Other polyanions include succinylated collagen, negatively charged chitosan derivatives, polyacrylic acid, chemically-modified dextans, sulfated polysaccharides, sodium alginate, albumin and the like. In general, the polyanion is a glycosaminoglycan.

"Nucleic acid" includes any nucleic acid which can be used for therapy of disease in humans or animals, or that can provide an advantageous result when coated on a medical device. Nucleic acid includes any of a variety of oligonucleotides, antisense oligonucleotides, plasmids, deoxyribonucleic acids (DNA), ribonucleic acids (RNA), expression vectors, ribozymes, and the like. Nucleic acid further includes any of a variety of constructs including nucleic acid compositions, such as synthetic nucleic acid compositions. The nucleic acid may be single-stranded or double-stranded, and may be linear or circular, such as a plasmid. The nucleic acid construct may also include other components, such as membrane disruption promoting components, promoters, regulatory elements, adenoviruses and the like. The nucleic acid may be employed, inter alia, to provide (i) a genetic template for proteins that function as prophylactic agents, (ii) a genetic template for proteins that function as therapeutic agents, (iii) a genetic template for proteins that function as immunizing agents, (iv) replacement copies of defective, non-functional or missing genes, (v) an antisense molecule, (vi) a genetic template for antisense molecules, (vii) a genetic template for ribozymes, or any combination or permutation of the foregoing. In one embodiment, the nucleic acid optionally includes regulatory sequences for transcription and translation in target cells. In another embodiment, such as for antisense molecules and ribozymes, the nucleic acid optionally includes regulatory sequences for production of copies of the molecules encoded by the nucleic acid.

In the following discussion and examples, "$\mu$L" means microliter, "mL" means milliliter; "L" means liter, "$\mu$g" means microgram, "mg" means milligram, "g" means gram, "mol" means moles, "M" means molar concentration, "Me" means methyl; "Bn" means benzyl, "nBu$_4$NI" means tetrabutyl-ammonium iodide, "° C." means degrees Centigrade. All percentages are in percent by weight unless otherwise indicated.

In general, both the polycation and polyanion must be selected such that (i) the polycation will form a condensate with nucleic acid by means of electrostatic interaction, and (ii) that sufficient net charge remains on the cationic condensate that the condensate binds to the polyanion by means of electrostatic interaction.

The polyanion, and any substrate or attachment component, may be adsorbed to biodegradable and non-biodegradable materials including stainless steel, titanium, platinum, tungsten, ceramics, polyurethane, poly tetrafluoroethylene, extended poly tetrafluoroethylene, polycarbonate, polyester, polypropylene, polyethylene, polystyrene, polyvinyl chloride, polyamide, polyacrylate, polyurethane, polyvinyl alcohol, polycaprolactone, polylactide, polyglycolide and copolymers of any two or more of the foregoing, siloxanes such as 2,4,6,8-tetramethylcyclo-tetrasiloxane, and natural and artificial rubbers.

The polyanion, and any substrate or attachment component, may be applied to three-dimensional matrices, including rods, coils, balloons, tubes, sheets, pins, screws, threads, braids, beads, particles, spheres, or a combination thereof.

The nucleic acid condensate complex may be a particle, aggregate, or other complex of a polycation nucleic acid binding agent and the nucleic acid. The binding agent may be a natural DNA-binding protein, recombinant DNA-binding protein, or DNA-binding compound that results in nucleic acid condensation.

Examples of medical devices with which this invention may be employed include sutures, graft materials, wound dressings, wound coverings, nerve growth guides, bone waxes, aneurysm coils, embolization particles, microbeads, stents, dental implants and bone prosthesis. The nucleic acid component may be applied singly, in combination, or in specified or restricted areas of a device surface.

Disease states wherein the invention may be of particular use include ischemia, cancer, restenosis, neural damage, myocardial infarction, peripheral vascular occlusion, and kidney ischemia.

In one embodiment, there is provided a nucleic acid condensate construct that is based on the use of heparin conjugated to silyl-type prosthetic units. The silyl-heparin is adsorbed onto surfaces by hydrophobic interaction via the prosthetic unit and is then used as a solid phase adsorbent for polycation condensed nucleic acid.

In another embodiment, there is provided an adenovirus that contains a heparin-binding domain that allows binding of the adenovirus to the heparin contained within the silyl-type prosthetic units. The silyl-heparin is adsorbed onto surfaces by hydrophobic interaction via the prosthetic unit and is then used as a solid phase adsorbent for the adenovirus that contains a heparin-binding domain. Wickham et al., *Nat. Biotechnol.* 11:1570–3 (1996) described the construction of an adenovirus that contains a heparin-binding domain that targets the virus to broadly-expressed heparin-containing cellular receptors. The adenovirus delivered genes to multiple cell types at markedly higher efficiencies than unmodified adenoviruses. These investigators did not describe, however, the use of the adenovirus to bind to heparin on medical devices or to silyl-heparin complexes, as in this invention. A key advantage of the method of this invention is that all the coating steps are performed by adsorption thereby allowed preparation of surfaces by "dip-coating". Another key advantage is that the heparin is not directly covalently bound to the surface, and as a consequence the complex of silyl-heparin and the nucleic acid condensate is more subject to efflux and more effective biological effect.

In one embodiment, silyl-heparin is coated on the exterior surface of a stent mounted on a balloon catheter. Immediately before in vivo use, the stent is immersed in a solution containing polycation-condensed nucleic acid, thereby allowing the polycation-condensed nucleic acid to bind to the stent. The stent is advanced into the patient using conventional techniques such as over a guiding catheter with an advancing catheter or element. The stent includes a mechanism radially expanding the stent to cause the polycation-condensed nucleic acid on the exterior surface of the stent to become juxtaposed in the artery wall, thereafter permitting the nucleic acid to undergo transfection over a period of time.

In yet another embodiment, the invention provides a method for administering gene therapy to a patient, comprising the steps of:

(a) advancing a balloon catheter having a balloon coated with silyl-heparin and one or more species of polycation-condensed nucleic acid into an artery of a patient to a desired administration site;

(b) inflating the balloon to pressure sufficient to cause the silyl-heparin and polycation-condensed nucleic acid to transfer to the artery wall; and (c) thereafter withdrawing the balloon catheter from the artery.

In one aspect, the invention provides a complex of Formula I:

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, n is a number from 1 to about 10, and x is a number from 1 to about 30. The polyanion may be any polyanion as disclosed herein, including but not limited to heparin, which is covalently joined through $R_3$. Attached to the polyanion, preferably through electrostatic interaction, is a condensate, such condensate including nucleic acid, and in a preferred embodiment including a polycation and nucleic acid condensate.

These and other aspects of the present invention are described further in the description and examples of the invention which follow.

Figure 1:
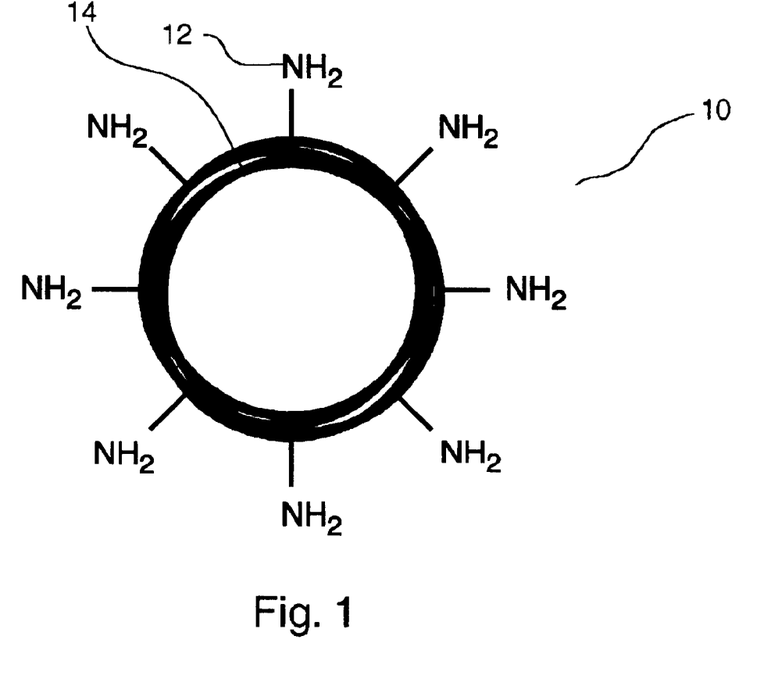
FIG. 1 depicts a polycation and nucleic acid condensate.
Figure 2:
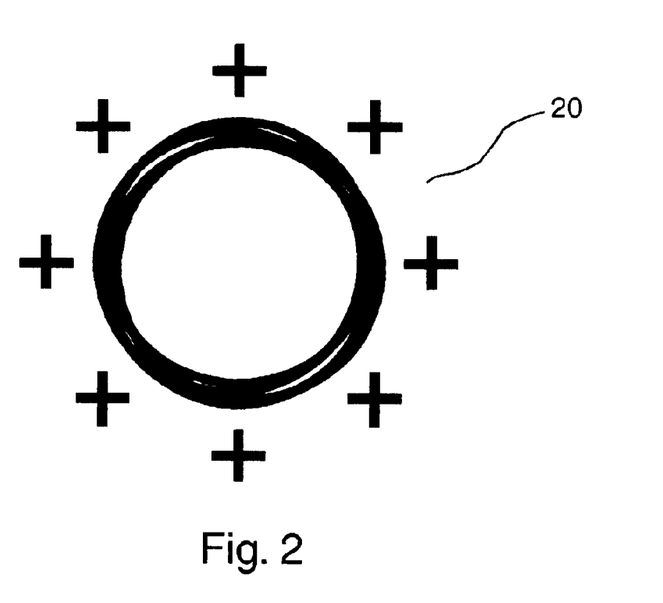
FIG. 2 depicts a polycation and nucleic acid condensate.

In FIG. 1 a condensate 10 of a polycation and nucleic acid is depicted. The polycation may be any polymeric cation, such as polylysine, polyornithine, polyarginine, a histone protein, polyethylenimine, or, in general, any cationic homopolymer or heteropolymer. The polycation and nucleic acid form polyplex 14 which has externally accessible —$NH_2$ groups 12, providing a net positive charge to condensate 10. The nucleic acid may be single-stranded DNA, double-stranded DNA, RNA or the like, including engineered constructs with one or more functions of nucleic acids. FIG. 2 depicts a simplified condensate 20 wherein the net positive charges are depicted.

Figure 3:
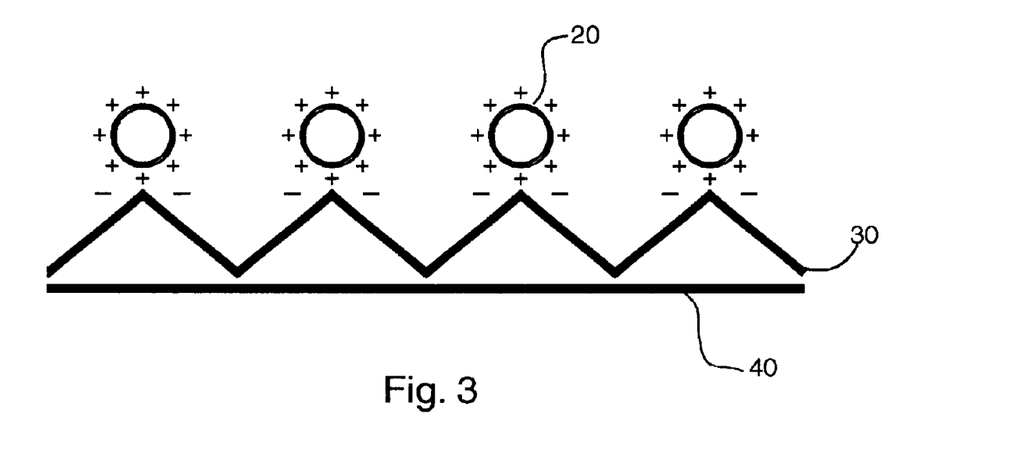
FIG. 3 depicts a coating composition of this invention applied to a surface.

FIG. 3 depicts one embodiment of this invention. Surface 40 is provided, which surface may be a contacting surface of a medical device, including preferably a medical device for in vivo use. Surface 40 may be made of any material suitable for medical devices, including metals, polymers, ceramics, glasses and the like. Attached to surface 40 is polyanion substrate 30. Polyanion substrate 30 may include any polyanion as defined herein. In one preferred embodiment, polyanion substrate 30 is heparin. Polyanion substrate 30 is attached to surface 40 by any means, such as hydrophobic bonding interaction, covalent bonds, electrostatic interaction or the like. Polyanion substrate 30 may be attached to surface 40 through one or more intermediate groups, which intermediate groups may attached by any means. Thus it is contemplated that an intermediate group may be attached to surface 40 by one means, such as hydrophobic bonding, and the polyanion substrate 30 attached to the intermediate group by another means, such as through a covalent bond. In one preferred embodiment, attachment of polyanion substrate 30 to surface 40 is by hydrophobic bonding interactions, optionally employing one or more intermediates. Condensate 20 is bound to polyanion substrate 30 by non-covalent means, and in a preferred embodiment, by electrostatic interaction.

Figure 4:
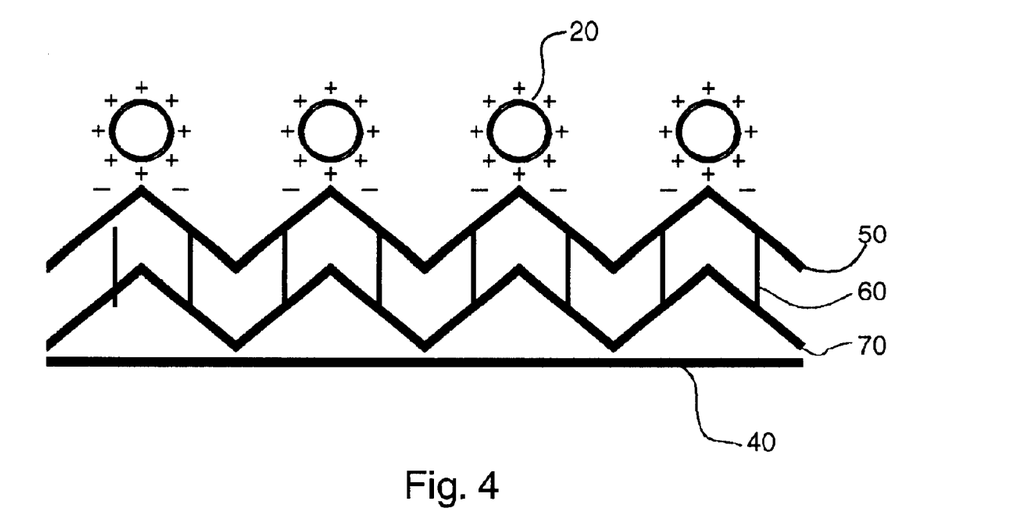
FIG. 4 depicts a coating composition of this invention, such composition including a silyl moiety having covalently bound thereto a polyanion, applied to a surface.

In an alternative embodiment, as depicted in FIG. 4, there is provided silyl moiety 70 that is bound to surface 40 by means of hydrophobic bonding interactions. Polyanion 50 is bound to silyl moiety 70 by means of covalent bond 60. Polyanion 50 is characterized in that it can be covalently bonded to silyl moiety 70 through an N or O, or optionally through a mix of N and O. Condensate 20 is bound to polyanion 50 by non-covalent means, and in a preferred embodiment, by electrostatic interaction.

Silyl-Heparin Compositions

In one embodiment, heparin is employed as the polyanion, and is bound to a silyl substrate by means of a covalent bond. The silyl substrate is, in turn, bound by hydrophobic interaction to the medical device surface.

The silyl-heparin compositions of the present invention include a covalent complex of one or more hydrophobic silyl moieties with heparin. Heparin is a mixture of variably sulfated polysaccharide chains composed of repeating units of D-glucosamine and either L-iduronic or D-glucuronic acids. Any suitable form of heparin may be employed in the reaction. A variety of salts of heparin and heparin derivatives are known in the art. For example, conventional salts of heparin include sodium heparin, calcium heparin, magnesium heparin, and potassium heparin. Heparin derivatives include, but are not limited to ammonium heparin, benzalkonium heparin, and the like. Sodium heparin is a preferred form of heparin for preparing the covalent complexes according to the present invention. All of the foregoing are included within the definition of "heparin" given above, together with salts and derivatives thereof.

The silyl moiety is represented by Formula I wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, and n is a number from 1 to 10. As will be apparent to those skilled in the art, $R_3$ is an N or O atom in the heparin molecule, and the unoccupied bond from $R_3$ signifies the attachment of the silyl moiety to the heparin molecule. Thus, the hydrophobic silyl moiety is capable of attachment to the heparin molecule at either an O atom of an alcohol (i.e., hydroxyl) or an N atom of an amine.

Heparin comprises many repeating units containing amine and hydroxyl functional groups which can be the site for attachment of the hydrophobic silyl moiety to the heparin molecule. Accordingly, one embodiment of the present invention contemplates the attachment of more than 1 hydrophobic silyl moiety to a single heparin molecule. As many as 30 or more hydrophobic silyl moieties of Formula I, and as few as 1 hydrophobic silyl moiety, may be attached to a single heparin molecule to achieve the covalent complex employed in the heparin coating compositions of the present invention. In one embodiment of the present invention, between 2 and 25 hydrophobic silyl moieties are attached to a single heparin molecule. In another embodiment, between 5 and 20 hydrophobic silyl moieties are attached to a single heparin molecule. In another embodiment, between 7 and 15 hydrophobic silyl moieties are attached to a single heparin molecule. In a preferred embodiment, 7 or 8 hydrophobic silyl moieties are attached to a single heparin molecule. In another preferred embodiment 12 hydrophobic silyl moieties are attached to a single heparin molecule.

As disclosed herein, the silyl-heparin complex is bound to the contacting surface of a medical device by means of hydrophobic interaction between the hydrophobic silyl moiety and the contacting surface, which is preferably also hydrophobic. The strength of the attachment, and the disassociation rate of silyl-heparin complexes from the contacting surface, is determined by at least three factors: the number of silyl units per silyl moiety (i.e., where n is a number between 1 and about 10), the number of silyl moieties per single heparin molecule (i.e., where x is a number between 1 and about 30), and the degree of hydrophobicity of the contacting surface. For applications where minimal or functionally no disassociation is desired, such as wherein disassociation of the condensate is desired without disassociation of the silyl-heparin complex, the number of silyl units per silyl moiety and the number of silyl moieties per heparin molecule may each be increased to the optimal number for maximal binding strength. Similarly the contacting surface may be selected so as to provide optimal hydrophobic binding with the silyl moieties. For applications where controlled release of the entire silyl-heparin-condensate over time is desired, fewer silyl units per silyl moiety or fewer silyl moieties per heparin molecule, or both, are selected, or a contacting surface providing decreased hydrophobic binding to the silyl moiety is selected, or a combination thereof, such that the desired release over time in vivo is obtained.

In those embodiments wherein more than one hydrophobic silyl moiety is attached to a single heparin molecule, the hydrophobic silyl moieties may be attached either through the amine of heparin (e.g., where $R_3$ is N) or through the hydroxyl group of heparin (e.g., wherein $R_3$ is O). In other words, some of they hydrophobic silyl moieties may be attached to the heparin molecule via bonding at the amine groups of heparin, while other hydrophobic silyl moieties are attached to the heparin molecule via bonding at the hydroxyl groups of heparin. It is also possible for all of the hydrophobic silyl moieties to be consistently attached to heparin via one or the other of the amine (e.g., $R_3$ in all hydrophobic silyl moieties is N) or the alcohol (e.g., $R_3$ in all hydrophobic silyl moieties is O).

The bonds between the hydrophobic silyl moieties and the heparin molecule that effect the attachment of the silyl moieties to the heparin molecule are covalent bonds. Thus, the coating compositions of the present invention do not rely upon ionic interactions between heparin and the hydrophobic moiety. Rather, the hydrophobic moieties are bonded to the heparin molecule by covalent bonding through either the amine or hydroxyl groups (or possibly a combination of both amine and hydroxyl groups when two or more hydrophobic silyl moieties are attached a single heparin molecule). Because the hydrophobic silyl moiety is bound to the heparin molecule through covalent bonding, the present invention overcomes one weakness of conventionally known heparin coatings. Specifically, the problem of heparin leaching from the coating as a result of the breaking of the ionic bond between heparin and the group which attaches heparin to the surface is overcome by avoiding reliance upon ionic bonding interactions between heparin and the binding group. In the present invention, the covalent bonds between the hydrophobic silyl moieties and the heparin molecule in the coating composition are not disrupted by the presence of ionic species in the blood with which the coated surface will come into contact.

The covalent complex according to the present invention can be prepared according to the following Scheme 1.

Scheme 1 wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, or n is a number from 1 to about 10, and x is a number from 1 to about 30.

Generally, the first intermediate, $R_1(Si(R_2)_2CH_2)_nCl$, wherein n is 1, is produced by reacting an alkyl or aryl magnesium chloride with a chloro(chloromethyl)-dialkyl silane or chloro(chloromethyl)diaryl silane in the presence of tetrahydrofuran (THF). The alkyl or aryl magnesium chlorides used as starting materials are commercially available, and include, for example, benzyl magnesium chloride. Chloro(chloromethyl)dialkyl silanes and chloro (chloromethyl)diaryl silanes are commercially available and include, for example, chloro(chloromethyl)dimethyl silane. The reaction is exothermic, and is typically conducted at temperatures of about 10° C. or less. The reaction is carried out for a sufficient period of time to yield about 80–90% product. Typically the reaction is conducted over a period of from about 2 to 15 about 24 hours.

First intermediates wherein n is 2 or higher can be produced using a Grignard reaction involving the reaction of the first intermediate wherein n is 1 with $ClSi(R_2)_2CH_2Cl$. This Grignard reaction can be repeated any number of times to achieve the desired value for n in the first intermediate. The reaction is carried out in the presence of a catalytic amount of iodine and THF.

The first intermediate (wherein n is 1–10) is converted to the second intermediate, $R_1(Si(R_2)_2CH_2)_nOH$, by reacting the first intermediate with potassium acetate (KOAc) in dimethyl formamide (DMF), at a temperature of above about 120° C., and preferably about 135° C. for between 12 and 24 hours. The product of this reaction is then reacted with sodium methoxide (NaOMe) in methanol (MeOH) under reflux for about 2 hours to achieve the second intermediate.

The second intermediate is converted to the last intermediate, $R_1(Si(R_2)_2CH_2)_nOCO_2N(COCH_2)_2$, by a two-step reaction process. In the first step, the second intermediate is reacted with triphosgene and sodium carbonate in methylene chloride at a temperature of less than 10° C., and preferably about 0° C. The product of this reaction is reacted with N-hydroxysuccinimide and triethylamine ($Et_3N$) in methylene chloride at a temperature of less than 10° C., and preferably about 0° C.

The final intermediate is covalently conjugated to heparin by reacting heparin with the final intermediate in a suitable solvent (e.g., water/dimethyl formamide) at a pH of about 8.0 to 9.0, and preferably about 8.5. The pH of the reaction is controlled by the addition of base such as sodium hydroxide, as needed. Alternatively and preferably, a slight excess of 4-dimethylaminopyridine (DMAP) can be used as base for the conjugation reaction with heparin. Using these general methods, the covalent silyl-heparin complexes of the present invention can be produced. The covalent complexes have the general Formula II:

II wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O of heparin, n is a number from 1 to about 10, and x is a number from 1 to about 30.

Preferred complexes include those complexes wherein $R_1$ of the hydrophobic silyl moiety is aryl. In one preferred embodiment, $R_1$ is benzyl. In one preferred embodiment, each $R_2$ is alkyl. In one particularly preferred embodiment, each $R_2$ is selected from the group consisting of methyl, ethyl, propyl, and isopropyl, particularly methyl. In one preferred embodiment, n is a number from 2 to 3.

Specific examples of covalent complexes according to the present invention include but are not limited to [benzyl-bis (dimethylsilylmethyl)]-(N-heparinyl)-carbamate, [benzyl-tris(dimethylsilylmethyl)]-(N-heparinyl)-carbamate, and dodecyl[benzyl-bis(dimethylsilylmethyl)]-(N-heparinyl)-carbamate. Although these three specific covalent complexes are examples of currently preferred covalent complexes having the general Formula II above, other specific examples of such complexes will be apparent to those skilled in the art and are contemplated by the instant invention.

The silyl-heparin coatings of the present invention include the silyl-heparin covalent complexes described above. In addition to the silyl-heparin covalent complex, the coating composition may also include one or more solvents that facilitate the processes of applying the composition to the surface. Suitable solvents include those which at least partially solubilize the covalent complex, and which preferably do not interfere with the anti-thrombogenic activity of heparin. Examples of solvents which may be employed in the coating compositions of the present invention include but are not limited to aqueous solvents, alcohols, nitriles, amides, esters, ketones, ethers, and the like. "Aqueous", with reference to solutions or solvents, refers to solutions or solvents that consist primarily of water, normally greater than 90% water by weight, and includes essentially or substantially pure water. For example, an aqueous solution or solvent can be distilled water, tap water, or the like. However, an aqueous solution or solvent can also include water having substances such as pH buffers, pH adjusters, organic and inorganic salts, alcohols (e.g., ethanol), sugars, amino acids, or surfactants incorporated therein. The aqueous solution or solvent may also be a mixture of water and minor amounts of one or more co-solvents, including agronomically suitable organic co-solvents, which are miscible therewith, or may form an emulsion therewith. Examples of suitable alcohol solvents include but are not limited to methanol, ethanol, propanol, isopropanol, hexanol, as well as glycols such as ethylene glycol and the like. Examples of suitable nitrites include acetonitrile, propionitrile, butyronitrile, benzonitrile and the like. Examples of suitable amides include formamide, N,N-dimethylformamide, N,N-dimethylacetamide and the like. Examples of suitable esters include methyl acetate, ethyl acetate and the like. Examples of suitable ketones include acetone, methyl ethyl ketone, diethyl ketone and the like. Examples of suitable ethers include diethyl ether, tetrahydrofuran, dioxane, dimethoxyethane and the like. Any two or more of any of the foregoing solvents may be utilized in the coating composition as well. Currently preferred solvents include water, particularly distilled water, isopropanol, acetonitrile, and combinations of any two or more of these solvents.

In one preferred embodiment, the silyl-heparin covalent complex is solubilized in solvent to achieve a concentration of between about 0.01 and about 10 percent by weight, preferably between about 0.1 and about 1 percent, and more preferably about 0.125 percent.

In addition to the foregoing solvents, the silyl-heparin coating compositions of the present invention may also include therein various conventional additives. Examples of additives which may be incorporated into the compositions of the present invention include but are not limited to benzalkonium, 4-dimethylaminopyridinium, tetrabutylammonium halides, and the like.

Contacting Surfaces of Medical Devices

The coatings may be applied to any of a wide variety of contacting surfaces of medical devices. Contacting surfaces include, but are not limited to, surfaces that are intended to contact blood, cells or other bodily fluids or tissues of a mammal, including specifically a human. Suitable contacting surfaces include one or more surfaces of medical devices that are intended to contact blood or other tissues. The medical devices include sutures, graft materials, wound dressings, wound coverings, bone waxes, bone prostheses, aneurysm coils, embolization particles, microbeads, stents, catheters, shunts, grafts, artificial blood vessels, nerve-growth guides, artificial heart valves, prosthetics, pacemaker leads, in-dwelling catheters, cardiovascular grafts, bone replacement, wound healing devices, cartilage replacement devices, urinary tract replacements, orthopedic implants, opthalmic implants and other medical devices known in the art. Other examples of medical devices that would benefit from the application of the present invention will be readily apparent to those skilled in the art of surgical and medical procedures and are therefore contemplated by the instant invention. The contacting surface may include a mesh, coil, wire, inflatable balloon, or any other structure which is capable of being implanted at a target location, including intravascular locations, intralumenal locations, locations within solid tissue, and the like. The implantable device can be intended for permanent or temporary implantation. Such devices may be delivered by or incorporated into intravascular and other medical catheters.

Suitable contacting surfaces include metals such as stainless steel, nitinol, titanium, tungsten, platinum, graphite and metal alloys; ceramics; any of a variety of polymeric materials such as polyvinyl chloride, polyethylene, polylactide, polyglycolide, polycaprolactone, polymethyl methacrylate, polyhydroxylethyl methacrylate, polyurethane, polystyrene, polycarbonate, dacron, polytetrafluoroethylene and extended polytetrafluoroethylene (Teflon®), related fluoropolymer composites (Gore-Tex®), polyester, polypropylene, polyamide, polyacrylate polyvinyl alcohol and copolymers of any two or more of the foregoing; siloxanes such as 2,4,6,8-tetramethylcyclotetrasiloxane; natural and artificial rubbers; and glass. In general, the contacting surface that may be coated with a silyl-heparin-condensate complex of the present invention includes any surface that has an affinity or attraction to the hydrophobic silyl moiety. Such surfaces are typically hydrophobic surfaces.

In one embodiment, the contacting surface may be a biodegradable or bioerodible material. Biodegradable or bioerodible materials are known in the art, and include polyanhydrides, polyglycolic acid, polylactic/polyglycolic acid copolymers, polyhydroxybutyrate-valerate and other aliphatic polyesters. Biodegradable implantable materials are described in U.S. Pat. Nos. 5,656,297; 5,543,158; 5,484,584; 4,897,268; 4,883,666; 4,832,686; and 3,976,071. In one embodiment, a bioabsorbable polymeric contacting surface is made from a biocompatible polymeric material such as polycaprolactone, poly(D,L-lactide), poly(L-lactide), polyglycolide, poly(dioxanone), poly(glycolide-co-trimethylene carbonate), poly(L-lactide-co-glycolide), poly(D,L-lactide-co-glycolide), poly(L-lactide-co-D,L-lactide) or poly(glycolide-co-trimethylene carbonate-co-dioxanone). In one embodiment, the persistence of the bioabsorbable polymeric structural component within a living organism is in excess of the anticipated period over which the nucleic acid present in the condensate will provide a therapeutic effect, and is preferably in excess of at least two such periods.

Application of Silyl-Heparin Complex

The silyl-heparin complex may be coated onto any of the contacting surfaces as set forth above. Any suitable method for applying the silyl-heparin complex to the surface may be employed. One suitable method for applying the silyl-heparin complex to the contacting surface is by dipping the contacting surface into a coating composition containing the silyl-heparin complex of the present invention. A liquid coating composition containing the silyl-heparin complex of the present invention may be prepared using any of the solvents described above. The surface is dipped or immersed into a bath of the coating composition. Typically, the dipping process is carried out at elevated temperatures, such as between about 30° C. and about 80° C., and for a defined period of time, such as for a period of between about 5 and about 20 minutes, preferably about 10 minutes. Thereafter, the surface may be allowed to remain in contact with the coating composition containing the silyl-heparin complex for a period of between about 15–60 minutes, preferably about 20 minutes, at room temperature.

Another method that may be employed for coating or applying the coating compositions of the present invention onto a contacting surface includes use of pumping or spraying processes. In a pumping process, a coating composition having a concentration of between 0.05 and about 5 percent (w/v) silyl-heparin complex is pumped through that portion of a medical device including a contacting surface for about 30 minutes. Thereafter any excess coating composition may be washed out with water or saline. Similarly, the contacting surface may be coated with the coating composition by spraying.

Following coating, the resulting silyl-heparin complex coated surface is typically washed with water or other aqueous solutions prior to drying. Advantageously, the foregoing methods for applying the coating composition to a surface are relatively quick, commercially feasible and cost-effective. They require no special equipment or special technical training, and can be applied to devices with complex surface geometries. Thus the silyl-heparin complex may be applied to any contacting surface, including three-dimensional matrices, rods, coils, tubes, sheets, pins, screws, threads, braids, beads, particles, spheres and combinations thereof.

The hydrophobic interaction between the hydrophobic contacting surface and the hydrophobic silyl moieties of the silyl-heparin complex forms a bond between the silyl moiety of the silyl-heparin complex and the surface. This hydrophobic interaction is sufficiently strong so as to provide a reasonable stable bond between the covalent complex and the surface. Advantageously, and depending in part on the hydrophobicity of the material of the contacting surface, a definable disassociation rate may be obtained, such that a given percentage of silyl-heparin complexes, together with the condensate bound to heparin, disassociate from the contacting surface, thereby providing for local or regional delivery of the condensate over a period of time. Such disassociation rate may be determined, in part, by the number of silyl units per silyl moiety or the number of silyl moieties bound to each heparin molecule, or both, and accordingly such numbers are selected based, in part, on the desired disassociation rate.

Nucleic Acid and Polycation Condensate

Polycation and nucleic acid polyplexes can be made under concentrated conditions, such as DNA at a concentration of about 87 nM, using a step dialysis protocol that allows a change in salt concentration from about 2 M to about 0.15 M. In such a method the ratio of polycation to DNA is typically between about one to two and one to twenty. Although DNA-containing polyplexes can be formed by this procedure, a certain amount of the polyplex may precipitate because of the high DNA and polycation concentration. Polyplexes can be formed efficiently in dilute DNA concentrations, such as DNA at a concentration of about 3 nM, in 0.15 M salt without precipitation of the DNA. In this method the ratio of polycation to DNA is again typically between about one to two and one to twenty. While the low DNA concentration does not allow for use directly in many in vivo applications, it may be employed in the present invention as the polyplex complexes to the polyanion bound to the medical device surface, and thereby concentrates the polyplex on the device surface.

In another embodiment, a silyl-heparin-nucleic acid and polycation condensate complex coating is used on microparticles for local and transient delivery of nucleic acid to increase collateral blood flow and to increase angiogenesis in ischemic tissue. Microparticles are made, such as by homogenizing a methylene chloride solution containing 3% polylactide:polyglycolide (PLGA) with a 2% aqueous polyvinyl alcohol solution to form an emulsion, sonicating the resulting mixture, and recovering particles by centrifugation after evaporation of the organic phase. After evaporation of methylene chloride, the PLGA microparticles are incubated in an aqueous solution containing 0.5% silyl-heparin, such as benzyl-bis(dimethylsilylmethyl) oxycarbamoyl-heparin, for 45 minutes. Unbound silyl-heparin is removed by centrifugation and rinsing in phosphate buffered saline. The silyl-heparin coated microparticles can then be resuspended in an aqueous buffer, such as a buffer containing dextrose, and optionally aliquoted into unit doses, lyophilized, and optionally sterilized by gamma radiation. The condensate of nucleic acid and polycation can then be incorporated immediately prior to use, by preparing the condensate in an aqueous solution, such as phosphate buffered saline containing 1% human serum albumin, and adding the condensate and solution to the lyophilized silyl-heparin coated microparticles. Alternatively, the microparticles are coated with a silyl-heparin-condensate complex, such as by coating with silyl-heparin and subsequently adding the polycation and nucleic acid condensate, incubating the microparticles with condensate at the desired concentration, removing unbound condensate by centrifugation and rinsing. The silyl-heparin-condensate complex coated microparticles are then optionally lyophilized and sterilized as described above. The silyl-heparin-condensate factor is released from the microparticles over a selected period of time, such as several days, thereby providing local and transient delivery of nucleic acid. In one embodiment, the length of the silyl moiety may be modified, by appropriately selecting "n" in Formula I or II and accordingly synthesizing the resulting silyl moiety, thereby modifying the rate of release or disassociation from the contacting surface of the microparticle, and thus controlling bioavailability in vivo. Similarly, the number of silyl moieties per heparin molecule may be modified, by appropriately selecting "x" in Formula I or II, thereby also modifying the rate of release or disassociation from the contacting surface of the microparticle, and thus controlling bioavailability in vivo.

The nucleic acid is selected specific for an application consonant with the medical device. For example, a suture may have a silyl-heparin-condensate coating complex applied thereto, where the nucleic acid is DNA that promotes wound healing, such as EGF. A stent may similarly have a nucleic acid that inhibits restenosis. A medical device placed in or adjacent to a tumor may have a silyl-heparin-condensate coating complex including a gene that encodes for an enzyme that activates an anticancer pro-drug, or alternatively that encodes for an antigen that in turn generates a protective immune response. Thus liposomal IL-2, IL-12 and tumor suppressor p53 genes may be employed. In one embodiment, a circular DNA plasmid is employed as the nucleic acid, which plasmid may range in size from several kilobases to over 50 kilobases in length. In other embodiments, much larger DNA constructs may be employed as nucleic acids.

It is also possible to modulate the disassociation rate of the condensate from the polyanion, such as heparin. Since the condensate and polyanion are bound by electrostatic interaction, varying the net charge of either the polyanion or the polycation forming a part of the condensate, or both, will result in a change in the disassociation rate. Thus depending on the specific application, a disassociation rate may be selected that provides optimal delivery of the nucleic acid to the intended target.

Industrial Applicability

The invention is further illustrated by the following non-limiting examples.

EXAMPLE 1

Method for Preparing Silyl-Heparin Covalent Complexes

Treatment of benzylmagnesium chloride 1 with chloro (chloromethyl)dimethysilane 2 gave benzyl(chloromethyl) dimethysilane 3 (n=1), all as shown in Scheme 2 below. Treatment of $3_n$ with magnesium gave the Grignard Reagent, which was treated with chloro(chloromethyl)dimethyl-silane again to give the homologous silyl compound $3_{n+1}$. The Grignard reaction can be repeated over and over again to obtain the desired chain-length for the silyl compound. The chloro-silyl compound 3, on treatment with potassium acetate, followed by trans-esterification of the corresponding acetate with basified methanol gave the alcohol 4. The alcohol 4, when treated with triphosgene gave the corresponding chloroformate, which on treatment with N-hydroxy-succinimide gave the N-hydroxy-succinimidyl-carbonate 5. The conjugation of heparin with 5 was achieved by treatment of heparin with 5 and 4-(dimethylamino) pyridine in 1:1 DMF/$H_2O$ to give the silylated heparin 6. Adjusting the molar ratios of the reactants controlled the number of prosthetic groups per heparin.

Scheme 2

Synthesis of Benzyl(chloromethyl)dimethylsilane, $3$ (n=1). Under an atmosphere of nitrogen, chloro (chloromethyl)dimethylsilane (100 mL, 0.744 mol) was added by syringe to THF (500 mL) and solution cooled to 0° C. with an ice/acetone bath. Benzylmagnesium chloride (2.0 M solution, 400 mL, 0.8 mol) was added dropwise over 2 hours. Care was taken to maintain the temperature below 10° C. until all the reagent was added. Thereafter, the ice bath was allowed to warm up to room temperature and the reaction mixture stirred overnight. Hexane (300 mL) was added and saturated aqueous $NH_4Cl$ (300 mL) added dropwise. The reaction mixture was transferred to a 2 L separatory funnel with more hexane (300 mL). After partitioning, the organic layer was washed with saturated aqueous $NH_4Cl$ (200 mL) and saturated aqueous NaCl (200 mL). The combined aqueous layers were backwashed with hexane (2×500 mL) and the combined organic layers dried over $MgSO_4$, evaporated on a rotary evaporator, and further concentrated under vacuum to give a colorless oil 162.0 g (109.5% yield). A quantitative yield was assumed with a purity of the crude product being 91.3%.

Grignard Reaction of $Bn(SiMe_2CH_2)_nCl$ $3_n$ and $ClSiMe_2CH_2Cl$ to give $Bn(SiMe_2CH_2)_{n+1}Cl$, $3_{n+1}$. Magnesium powder (7.5 g, 0.31 mol), a catalytic amount of Iodine and THF (100 mL) were placed in a 500 mL 3-necked flask equipped with a condenser-$N_2$ inlet, a septum and a thermometer. The mixture was heated to reflux briefly until the brown color of iodine disappeared. $Bn(SiMe_2CH_2)_nCl$ (0.2 mol) was added slowly by syringe and the reaction was initiated with a heat gun; an exothermic reaction was observed and the reaction flask was placed in an ice water bath momentarily until the exothermic reaction subsided. The residual reagent washed into the reaction mixture with THF (2×25 mL). The resulting gray mixture was heated to reflux for 24 hours. The reagent was then cooled to room temperature and cannulated into a pressure filter funnel where it was added directly into another 500 mL round bottom flask in which was placed a solution of $ClSiMe_2CH_2Cl$ (27.0 mL, 0.2 mol) in THF (50 mL) at room temperature. The pressure filter funnel with magnesium residue was washed into the reaction mixture with THF (2×25 mL). The reaction mixture was heated to reflux overnight. To the resulting gray suspension was added saturated aqueous $NaHCO_3$ (50 mL) and the resulting solution transferred to a 500 mL separatory funnel with hexane (200 mL). After partition, the organic layer was washed with saturated aqueous $NaHCO_3$ (50 mL) and saturated aqueous NaCl (50 mL). The combined aqueous layers were backwashed with hexane (2×100 mL), dried over $MgSO_4$, and extensively evaporated under vacuum to give an amber oil. The amber oil was purified by distillation to give colorless oil. Yields were over 80%.

Conversion of $Bn(SiMe_2CH_2)_nCl$ $3_n$ to $Bn(SiMe_2CH_2)_nOH$ $4_n$. $Bn(SiMe_2CH_2)_nCl$ (0.16 mol) was dissolved in DMF (300 mL) in a 1-L 3-necked flask. KOAc (50 g, 0.5 mol) was added followed by $nBu_4NI$ (4.0 g, 0.01 mol) and the reaction mixture was stirred in a 135° C. oil bath for 24 hours. The reaction mixture was worked up by cooling to room temperature and transferring to a 1 L separatory funnel with hexane (500 mL) and washed with saturated aqueous NaCl (3×100 mL). The combined aqueous layers was backwashed with hexane (3×300 mL) and the combined organic layers dried over $MgSO_4$ and evaporated to an amber oil, which was dissolved in MeOH (400 mL). A generous amount of freshly prepared NaOMe was added to adjust the pH to >10 and the reaction mixture heated to reflux for 2 hours. The reaction mixture was neutralized with AcOH, evaporated to dryness and chromatographed with silica gel in a 6.5×100 cm (height of silica 40 cm) flash column and eluted with 0–30% EtOAc/hexane to give the desired product, a slightly yellow oil. Yields were over 80%.

Conversion of $Bn(SiMe_2CH_2)_nOH$ $4_n$ to $Bn(SiMe_2CH_2)_n$—$OCO_2N(COCH_2)_2$ $5_n$. Triphosgene (60 g, 0.2 mol) was dissolved in $CH_2Cl_2$ (200 mL) and stirred at 0° C. under $N_2$ in a 1-L 3-necked flask equipped with thermometer, dropping funnel and $N_2$ inlet. $Na_2CO_3$ (65 g, 0.6 mol) was added followed by $Bn(SiMe_2CH_2)_nOH$ (0.13 mol dissolved in 200 mL of $CH_2Cl_2$) dropwise over 30 minutes. Thereafter, the ice/acetone bath was allowed to come to room temperature. The reaction mixture was stirred overnight, filtered through a sintered glass funnel, and the reaction vessel rinsed with $PhCH_3$ (200 mL). The solution was concentrated under vacuum to give a colorless oil. The oil was dissolved in $CH_2Cl_2$ (200 mL) and stirred in an ice bath under $N_2$. N-Hydroxysuccinimide (30 g, 0.26 mol) was added followed by $Et_3N$ (40 mL, 0.28 mol) dropwise over 15 minutes and the resulting cloudy mixture stirred at room temperature for one hour. The reaction mixture was diluted with hexane (200 mL), washed with saturated aqueous $NH_4Cl$ (3×100 mL), and the combined aqueous phases backwashed with hexane (2×200 mL). The combined organic phases were dried over $MgSO_4$ and concentrated under vacuum to give amber oil. The amber oil was chromatographed on silica gel in a 6.5×100 cm (height of silica 40 cm) flash column and eluted with 20–50% EtOAc/hexane to give an amber syrup. Yields are generally greater than 75%.

Conjugation of Heparin with $Bn(SiMe_2CH_2)_nOCO_2N(COCH_2)_2$ $5_n$ to give $6_{n,x}$. Heparin (ammonium ion-free, average molecular weight 10,000; 100 g, 10 mmol) was dissolved in $H_2O$ (500 mL) in a 2 L flask with stirring. DMF (400 mL) was added followed by DMAP (1.6× g, 13× mmol). $Bn(SiMe_2CH_2)_nO$—$CO_2N(COCH_2)_2$, $5_n$ (10× mmol) in DMF (100 mL) was added and the resulting milky mixture was allowed to stir at room temperature for >24 hrs. The reaction mixture was concentrated by evaporating most of the water followed by trituration with acetone (2 L). The white suspension was filtered through a sintered glass funnel to give a white solid residue. This crude material was purified by soxhlet extraction with acetone overnight to give a white powder. The yields were generally greater than 95%.

The average number of prosthetic units per molecule of heparin was estimated based on a comparison of the molar ratios of the hydrolyzed prosthetic unit benzyl-tris (dimethylsilyl-methyl)-OH and heparin as determined by use of dimethyl methylene blue. Heparin was detected using a commercially-available enzyme-linked assay that measures the heparin-induced inhibition of antithrombin/factor Xa as measured with a factor Xa specific chromogenic substrate.

EXAMPLE 2

Techniques for Applying Silyl-Heparin Coating Compositions to Surfaces.

The silyl-heparin complex of Example 1 was used as a coating solution as a 1% solution (w/v) in 60% aqueous ethanol. Materials were coated with silyl-heparin for 15 minutes at 370° C. The coated materials were then were rinsed extensively in water, air-dried, and stored until use.

In another embodiment, the silyl-heparin complex was dissolved in distilled water with gentle stirring, and an organic solvent added, such as isopropyl alcohol or acetonitrile, such that the organic solvent constituted approximately ⅔ of the volume, such as 100 mg of silyl-heparin complex of Example 1 solubilized in 27 mL of distilled water with gentle stirring, with 53 mL of isopropyl alcohol or acetonitrile then added, providing a resulting concentration of the silyl-heparin complex in solution of about 0.125%. In other embodiments, the resulting solution had a silyl-heparin complex concentration of between 0.01 and 10 percent based upon the weight of the solution. The material to be coated was dipped in the solution at elevated temperatures usually ranging from 30° C. to 50° C. for about 10 minutes, followed by standing in room temperature for about 20 minutes. The coated material was taken out of the coating solution and rinsed thoroughly with distilled water or saline solution prior to drying.

EXAMPLE 3

Stability of Heparin Coating Compositions on Surfaces Exposed to Ionic Environments Various surfaces coated according to Example 2 were evaluated for heparin activity after washing with 3% (by weight) sodium chloride solution. Surface heparin activity was measured using a commercially available kit for detecting heparin and the results reported in mIU/cm$^2$.

Results obtained from the evaluation of average heparin activity on various surfaces after washing with sodium chloride are set forth in Table 1 below. The concentration of the covalent complex in the coating solution was 0.25% (W/V).

TABLE 1

| Material Coated | Percent by volume of isopropyl alcohol in IPA/H$_2$O solvent | | | | | |
| --- | --- | --- | --- | --- | --- | --- |
| | 50% | 55% | 60% | 65% | 70% | 75% |
| | mIU of Heparin/Square Centimeter | | | | | |
| POLYCARBONATE | 6.8 | 8.0 | 17.6 | 16.3 | 14.7 | 14.9 |
| TMCTS | 0.4 | 3.8 | 3.5 | 2.0 | 1.1 | 2.4 |
| POLYESTER | 4.5 | 4.4 | 5.5 | 3.7 | 5.3 | |
| POLYVINYL CHLORIDE | 2.6 | 2.9 | 10.0 | 6.5 | 4.0 | 2.8 |
| STAINLESS STEEL | 12.9 | 13.1 | 8.3 | 11.0 | 12.9 | 13.8 |

EXAMPLE 4

Use of Different Silyl-Heparin-Adhesive Molecules

Silyl-heparin complexes were evaluated for ability to bind to several polycation molecules as shown in Table 2. Attachment of polycation molecules to silyl-heparin complex coated hydrogel-polystyrene plates was detected by staining with crystal violet. This method was used to verify that the polycation had bound to the silyl-heparin. All proteins were used at a concentration of 100 μg/mL in buffered saline. Serum was used without dilution. Statistical significance was assessed relative to the values from buffered saline using Student's t-test, with * indicating p<0.05 and *** indicating p<0.001.

TABLE 2

| Polycation Molecule | Average ± S.E. |
| --- | --- |
| Control (saline) | 0.05 ± 0.03 |
| albumin | 0.08 ± 0.00 |
| poly-L-ornithine | 0.92 ± 0.28* |
| poly-L-lysine | 1.18 ± 0.06*** |
| serum | 0.16 ± 0.02 |
| type VI collagen | 2.01 ± 0.08*** |

EXAMPLE 5

Preparation of Silyl-Heparin Complexes for use with Polycation and Nucleic Acid Condensates Silyl-Heparin was prepared as generally disclosed in Example 1, with 3 silyl units per silyl moiety. The average number of silyl moieties per molecule of heparin was estimated based on a comparison of the molar ratios of the hydrolyzed prosthetic unit benzyl-tris(dimethylsilyl-methyl)-OH and heparin as determined by use of dimethyl methylene blue. Heparin was detected using a commercially available enzyme-linked assay that measures the heparin-induced inhibition of antithrombin/factor Xa as measured with a factor Xa specific chromogenic substrate. The silyl-heparin complex was used in a coating solution at 1% solution (w/v) in 60% aqueous ethanol. Contacting surfaces were coated with silyl-heparin for 15 minutes at 37° C. The wells were rinsed extensively in water, air-dried, and stored until use.

EXAMPLE 6

Sutures Coated with Silyl-Heparin

Vicryl suture material was coated using a solution containing silyl-heparin complex as in Example 2. The suture material was then rinsed extensively, air-dried, mounted on 16 gage needles and stored until use, typically overnight.

EXAMPLE 7

Effect of Varying "x" and "n" on Disassociation

Silyl-heparin complexes of Formula II were synthesized by varying a) the silyl chain-length in the silyl moiety ("n"), and b) the number of silyl moieties per heparin molecule ("x"). The resident time of the silyl-heparin bound to stainless steel varied, with silyl-heparin complexes where n=4 having the longest resident time. Varying the number of silyl moieties per heparin molecule, studied over the range from x=2 to x=20 also affected the resident time of the silyl-heparin complex on stainless steel, with the longest resident time observed where x=4 to x=6.

EXAMPLE 8

EGF Gene for Would Healing

A suture of Example 6, coated with silyl-heparin, is dipped in a solution containing a polycation and nucleic acid polyplex condensate, formed by step dialysis of a polyanion and an EGF gene. The resulting coating on the suture is a silyl-heparin-condensate, wherein the condensate includes an EGF gene, thereby effecting enhanced wound healing by use of the suture.

EXAMPLE 9

Joint Prosthetic Medical Device

Blood and tissue contacting surfaces of a joint prosthetic medical device are coated with a silyl-heparin as in Example 2. The device is then dipped in a solution containing a polycation and nucleic acid polyplex condensate, formed by step dialysis of a polyanion and an gene expressing the DNA sequence for TGFβ-1. The resulting coating on the suture is a silyl-heparin-condensate, wherein the condensate includes the DNA sequence for TGFβ-1, thereby effecting enhanced articular cartilage healing.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A nucleic acid-containing coating composition for contacting surfaces of medical devices, said composition comprising a polyanion substrate having bound thereto by non-covalent means a condensate comprising a polycation and nucleic acid.

2. The composition according to claim 1 wherein the polyanion substrate is a glycosaminoglycan.

3. The composition according to claim 1 wherein the polyanion substrate is heparin.

4. The composition according to claim 3 wherein the heparin comprises heparan sulfate, hyaluronic acid, amino dextran, dextran sulfate, chondroitin sulfate, dermatan sulfate, a molecule including a mixture of variably sulfated polysaccharide chains composed of repeating units of D-glucosamine and either L-iduronic or D-glucuronic acids, or salts or derivatives of any of the foregoing.

5. The composition according to claim 1 wherein the polyanion substrate comprises collagen, negatively charged chitosan derivatives, polyacrylic acid, chemically-modified dextans, sulfated polysaccharides, sodium alginate or albumin.

6. The composition according to claim 1 wherein the polyanion complex binds to the contacting surfaces.

7. The composition according to claim 6 wherein the polyanion complex binds to the contacting surfaces via hydrophobic bonding interactions.

8. The composition according to claim 1 wherein said nucleic acid is double-stranded DNA, single-stranded DNA, or RNA.

9. The composition according to claim 1 wherein said polycation is a histone protein, polyornithine, polylysine, polyarginine or polyethylenimine.

10. The composition according to claim 1 wherein said condensate is directly bound to the polyanion substrate by electrostatic interaction.

11. A coating composition for contacting surfaces of medical device, said composition comprising a molecule of Formula I:

wherein $R_1$ is an $C_{1-18}$ alkyl or $C_{6-32}$ aryl group, each $R_2$ is independently selected from the group consisting of $C_{1-18}$ alkyl and $C_{6-32}$ aryl $R_3$ is N or O, n is a number from 1 to 10, and x is a number from 1 to about 30, bound to a heparin-activity molecule via a covalent bond, thereby forming a silyl-heparin covalent complex, with a condensate comprising a polycation and nucleic acid directly and non-covalently bound to the heparin-activity molecule.

12. The composition according to claim 11 wherein the silyl-heparin covalent complex binds to the contacting surfaces via hydrophobic bonding interactions.

13. The composition according to claim 11 wherein the silyl-heparin covalent complex has a disassociation rate from the contacting surface determined by the value of n and x.

14. The composition according to claim 11 wherein the heparin-activity molecule comprises heparin, heparan sulfate, hyaluronic acid, dextran, dextran sulfate, chondroitin sulfate, dermatan sulfate, or a molecule including a mixture of variably sulfated polysaccharide chains composed of repeating units of D-glucosamine and either L-iduronic or D-glucuronic acids or salts or derivatives of any of the foregoing.

15. The composition according to claim 11 wherein said nucleic acid is double-stranded DNA, single-stranded DNA, or RNA.

16. The composition according to claim 11 wherein said polycation is a histone protein, polyornithine, polylysine, polyarginine or polyethylenimine.

17. The composition according to claim 11 wherein said condensate is directly bound to the heparin-activity molecule by electrostatic interaction.

18. The composition according to claim 11 wherein the silyl-heparin covalent complex comprises [benzyl-bis(dimethylsilylmethyl)]-(N-heparinyl)-carbamate or [benzyl-tris(dimethylsilylmethyl)]-(N-heparinyl)-carbamate.

19. A medical device with at least one contacting surface for contacting bodily fluids, the surface having coated thereon a coating composition comprising a molecule of Formula I:

wherein
R₁ is an $C_{1-18}$ alkyl or $C_{6-32}$ aryl group,
each R₂ is independently selected from the group consisting of $C_{1-18}$ alkyl and $C_{6-32}$ aryl,
R₃ is N or O,
n is a number from 1 to 10, and
x is a number from 1 to about 30,
directly bound to a heparin-activity molecule via covalent bonding, thereby forming a silyl-heparin covalent complex, with a condensate comprising a polycation and nucleic acid directly and non-covalently bound to the heparin-activity molecule.

20. The device according to claim 19 wherein the silyl-heparin covalent complex binds to the surface via hydrophobic bonding interactions.

21. The device according to claim 19 wherein the silyl-heparin covalent complex has a disassociation rate from the surface determined by the value of n and x.

22. The device according to claim 19 wherein the heparin-activity molecule is heparin, heparan sulfate, hyaluronic acid, dextran, dextran sulfate, chondroitin sulfate, dermatan sulfate, or a molecule including a mixture of variably sulfated polysaccharide chains composed of repeating units of D-glucosamine and either L-iduronic or D-glucuronic acids, or salts or derivatives of any of the foregoing.

23. The device according to claim 19 wherein said nucleic acid is double-stranded DNA, single-stranded DNA, or RNA.

24. The device according to claim 19 wherein said polycation is a histone protein, polyornithine, polylysine, polyarginine or polyethylenimine.

25. The device according to claim 19 wherein said condensate is directly bound to the heparin-activity molecule by electrostatic interaction.

26. The device according to claim 19 wherein the silyl-heparin covalent complex comprises [benzyl-bis(dimethylsilylmethyl)]-(N-heparinyl)-carbamate or [benzyl-tris(dimethylsilylmethyl)]-(N-heparinyl)-carbamate.

27. The device according to claim 19 wherein the device is a blood gas exchange device, blood filter, artificial blood vessel, artificial valve, prosthetic, blood shunt, catheter, bone replacement, cartilage replacement, suture, graft, catheter or nerve growth guide.

28. A method for coating a contacting surface of a medical device with a nucleic acid-containing coating composition, comprising:

providing a hydrophobic silyl moiety of Formula I wherein
R₁ is an $C_{1-18}$ alkyl or $C_{6-32}$ aryl group,
each R₂ is independently selected from the group consisting of $C_{1-18}$ alkyl and $C_{6-32}$ aryl,
R₃ is N or O, and
n is a number from 1 to 10
binding said silyl moiety to a heparin-activity molecule via covalent bonding, wherein x is from 1 to about 30 for each heparin-activity molecule, thereby forming a silyl-heparin complex,
attaching the silyl-heparin complex to the contacting surface by hydrophobic interaction, and
attaching a condensate comprising a polycation and a nucleic acid to the heparin-activity molecule.

29. The method of claim 28 wherein the silyl-heparin complex has a disassociation rate from the contacting surface determined by the value of n and x.

30. The method of claim 28 wherein the heparin-activity molecule is heparin, heparan sulfate, hyaluronic acid, dextran, dextran sulfate, chondroitin sulfate, dermatan sulfate, or a molecule including a mixture of variably sulfated polysaccharide chains composed of repeating units of D-glucosamine and either L-iduronic or D-glucuronic acids, or salts or derivatives of any of the foregoing.

31. The method of claim 28 wherein said polycation is a histone protein, polyornithine, polylysine, polyarginine or polyethylenimine.

32. The method of claim 28 wherein said condensate is directly bound to the heparin-activity molecule by electrostatic interaction.

33. The method of claim 28 wherein the silyl-heparin covalent complex comprises [benzyl-bis (dimethylsilylmethyl)]-(N-heparinyl)-carbamate or[benzyl-tris(dimethylsilylmethyl)]-(N-heparinyl)-carbamate.

* * * * *

UNITED STATES PATENT AND TRADEMARK OFFICE
CERTIFICATE OF CORRECTION

PATENT NO. : 6,596,699 B2
DATED : July 22, 2003
INVENTOR(S) : Paul O. Zamora et al.

It is certified that error appears in the above-identified patent and that said Letters Patent is hereby corrected as shown below:

Column 21,
Lines 55 and 57, the words "polyanion complex" should read -- polyanion substrate --

Signed and Sealed this

Fifteenth Day of June, 2004

JON W. DUDAS
*Acting Director of the United States Patent and Trademark Office*